United States Patent [19]

Lewis, Jr.

[11] Patent Number: 4,982,730

[45] Date of Patent: Jan. 8, 1991

[54] ULTRASONIC WOUND CLEANING METHOD AND APPARATUS

[76] Inventor: Royce C. Lewis, Jr., 5233 19th St., Lubbock, Tex. 79407

[21] Appl. No.: 289,361

[22] Filed: Dec. 21, 1988

[51] Int. Cl.$^5$ .............................................. A61B 17/00
[52] U.S. Cl. ...................................... 128/24 A; 604/22
[58] Field of Search ................ 123/66, 24 A; 433/86, 433/119; 604/22

[56] References Cited

U.S. PATENT DOCUMENTS

| | | | |
|---|---|---|---|
| 3,433,226 | 3/1969 | Boyd | 128/24 A |
| 3,522,801 | 8/1970 | Robinson | 433/119 |
| 3,584,627 | 6/1971 | Fisher | 128/66 |
| 3,636,947 | 1/1972 | Balamuth | 128/24 A |
| 3,645,255 | 2/1972 | Robinson | 128/24 A |
| 3,921,635 | 11/1975 | Gauthier | 128/66 |
| 4,331,422 | 5/1982 | Heyman | 433/86 |
| 4,709,691 | 12/1987 | Lemons et al. | 128/66 |

FOREIGN PATENT DOCUMENTS

| | | | |
|---|---|---|---|
| WO85/02111 | 5/1985 | PCT Int'l Appl. | 128/24 A |
| 00618110 | 8/1978 | U.S.S.R. | 128/66 |
| 0839505 | 6/1981 | U.S.S.R. | 604/22 |
| 0878268 | 11/1981 | U.S.S.R. | 128/24 A |
| 1292772 | 2/1987 | U.S.S.R. | 128/24 A |

*Primary Examiner*—Kyle L. Howell
*Assistant Examiner*—John D. Zele
*Attorney, Agent, or Firm*—Marcus L. Bates

[57] ABSTRACT

An ultrasonic wound cleaning device having an annular transducer, an axial bore extends through the annular transducer through which liquid admixed with modifying agents can flow towards a surface to be treated. A handle, a cleaning head, and a collecting cone are arranged respectively to the transducer so that cleaning liquid can flow through the axial bore, into the collecting cone, through the cleaning applicator head, where the liquid containing ultrasonic energy is brought into intimate contact with the wound and causes unwanted matter to be dislodged and washed from the wound and suspended in the liquid, and the loosened matter subsequently is flushed out of and away from the wound. The invention further comprehends preparation of human bone whereby joint replacement with a prosthesis can be carried out in a more sophisticated manner than has heretofore been possible.

8 Claims, 3 Drawing Sheets

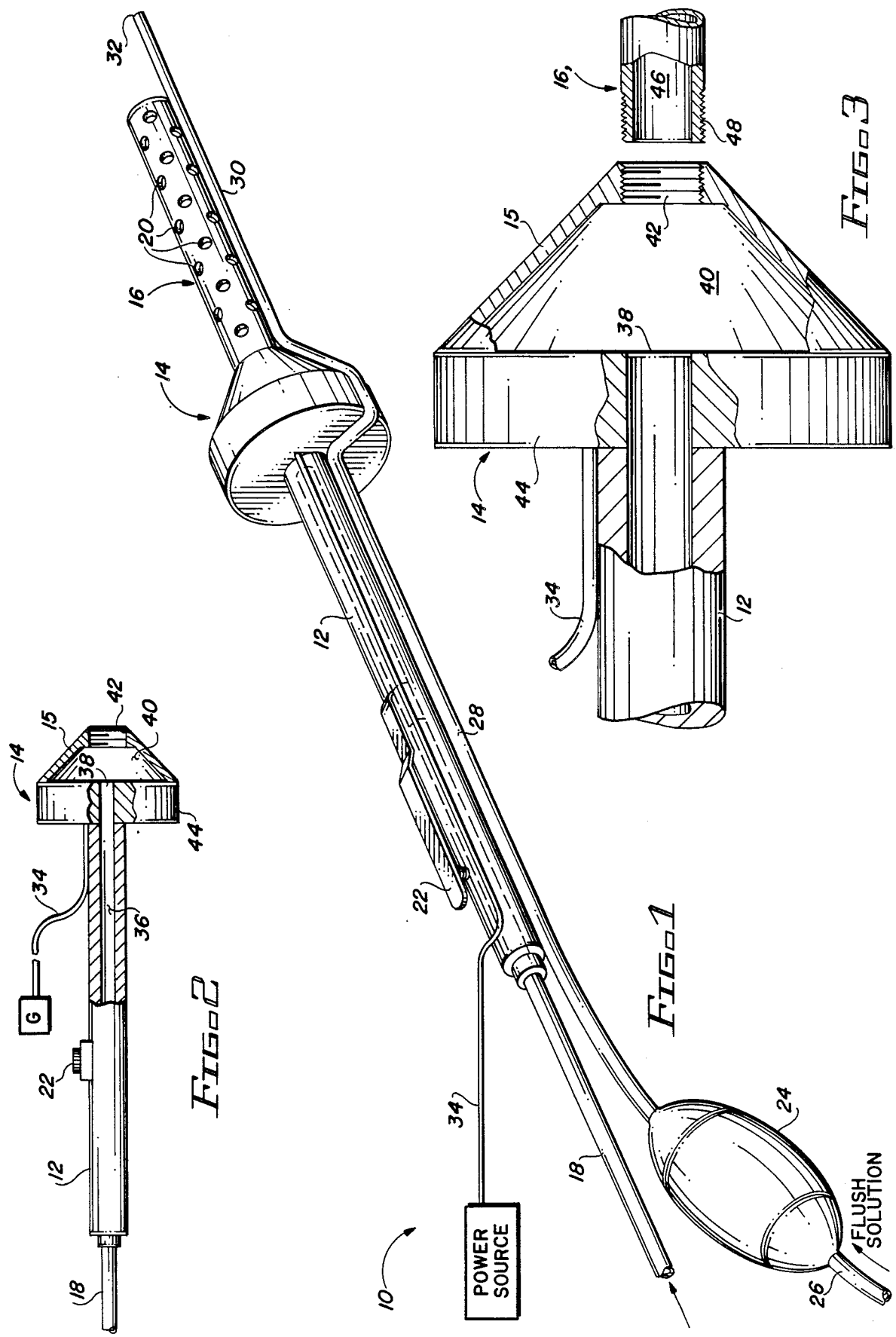

ULTRASONIC WOUND CLEANING METHOD AND APPARATUS

BACKGROUND OF THE INVENTION

This invention comprehends both method and apparatus for cleaning wounds with an ultrasonic cleaner and for surgically preparing bones to receive a prosthesis.

Ultrasonic cleaners are known to those skilled in the art as evidenced by the ultrasonically agitated liquid contained within a vat and used for cleaning jewelry. The jewelry is deposited directly into the vat where it is surrounded by the cleaning liquid which is agitated by ultrasonic energy. Rare and expensive jewelry can be cleaned safely by utilizing this unique cleaning method. The medical profession has discovered that a wounded hand, for example, can be placed into an ultrasonic cleaner, similar to the one used for cleaning jewelry, and that suitable detergents and antibiotics can be added to the liquid contained within the vat, to thereby clean the wound in a safe and remarkable manner.

This invention comprehends preparation of a joint whereby joint replacement with a prosthesis can be carried out in a more sophisticated manner than has heretofore been possible. For example, in substituting a prosthesis for a hip joint, the acetabulum or hip socket is reamed out down to healthy bleeding bone. The head of the femur or the hip joint ball is removed by cutting across the bone at the base of the neck, thus exposing the medullary cavity of the femur or thigh bone. The medullary canal is then reamed out with varying size reamers to fit the stem of the prosthesis that is to be used to supply the artificial ball for the ball and socket joint. Once the bed has been prepared, it is necessary to have a completely clean and dry field for use of the methyl methacrylate cement that is ordinarily used to hold the prosthetic components in place.

At the present time, there is not a completely satisfactory method available for use in cleaning out either the acetabular fossa or the medullary canal or femur. Various methods for achieving this operation have been used including irrigation, packing with sponges, and other similar methods, but most of these methods are not entirely satisfactory.

The present invention supplies a solution to this problem in that both the medullary canal of the bone and the acetabular hip joint socket can be cleaned out with a foam that is created by passing a solution of saline containing antibiotics through the central core of an ultrasound transducer resulting in a cavitation of the solution with the formation of a froth which has a tremendous and unexpected cleaning effect. The unusual cleaning affect of this ultrasound created froth is brought about by a mechanical cleansing action wherein transient energy from an ultrasound generator is imparted into a liquid and the liquid is placed into direct contact with the surface of the wound or bone, whereupon, as the stored energy is dissipated it cavitates the liquid while the liquid is in intimate contact with the prepared bone surface, for example, and thereby creates a highly desirable release of energy. This results in the attainment of several different desirable cleaning actions including the direct transference of energy directly to the wound surface as well as the release of energy as small bubbles are created and subsequently ruptured and the transfer of the surface tension energy to mechanically clean the surface of the bone. The apparatus further includes a small tube which is attached and runs down past the ultrasound nozzle so that it can be used to periodically flush out the unwanted debris which has been loosened by the ultrasonic foam.

In the cleansing of the acetabulum (hip socket) an attachment is provided which has a mushroom type configuration with small openings in it that will allow the ultrasonic created froth to act on the raw bleeding bone and thereby mechanically cleanse the surfaces of the bone in a similar manner. Irrigation can be done periodically with a syringe since the acetabulum is usually easily exposed. The same mechanism works for preparation of the bone for insertion of the components of the artificial knee joint replacement, or any other instances in which it is necessary to use methyl methacrylate cement. In some instances in which "pathologic" fractures occur through malignant tumor areas, the use of methyl methacrylate cement has been approved for use with some type of metallic internal fixation in order to secure solidarity of fixation of these fractures. In these instances, of course, the area in which the methacrylate cement is to be inserted must be completely clean and dry. These requirements are easily accomplished by the ultrasonic wound cleaner.

Another use of the present invention is that of a wound cleaner in acute trauma or in the treatment of dirty wounds. By removing the attachments used in carrying out the above method and allowing the ultrasonic created froth to emerge from the collecting chamber directly, the wound can be cleansed by moving or rubbing the instrument back and forth across the open area of the wound cavity and allowing the bubbles of the froth to come in contact with the structures lying in the depths of the open wound. This will be much better technically than local irrigation of the wound with syringes and certainly will be much kinder to tissue than the use of high pressure pumps which are now ordinarily employed for this particular need.

The ultrasonic wound cleaner of this invention is also useful in the emergency room where, on many occasions, less critical but nevertheless dirty and contaminated wounds need to be treated.

SUMMARY OF THE INVENTION

The present invention is directed to method and apparatus for cleaning a wound utilizing liquid that is being agitated with ultrasonic energy. More specifically, the present invention comprehends apparatus having a handle to which there is attached an ultrasonic transducer with the handle having a passageway which leads to an axial passageway formed centrally through an annular transducer. The other side of the transducer supports a cone having an apex spaced from the transducer in opposition to the handle and the cone is axially aligned with the passageway through the transducer. The apparatus of the present invention further comprehends alternant configurations of appliances that are removably affixed at the apex of the cone that enables liquid having ultrasonic energy contained therein to be directly placed in contact with the wound, whereby the cleaning liquid agitates contaminants and unwanted debris from the wound as the ultrasonic energy is released at the contaminated surfaces of the wound.

The method of the present invention comprehends flowing a cleaning liquid through an ultrasonic transducer and directly into the interior of a wound whereby the liquid simultaneously contacts the wound while it is absorbing energy from the transducer and dissipating the energy at the surfaces forming the interior of the wound.

Accordingly, a primary object of the present invention is the provision of ultrasonic apparatus for use in cleaning wounds.

Another object of this invention is the provision of apparatus for cleaning wounds with a liquid having ultrasonic energy contained therein.

A further object of this invention is the provision of ultrasonic transducer apparatus for releasing ultrasonic energy from a liquid while the liquid is in direct contact with the interior surface of a wound.

Another and still further object of this invention is the provision of a method of cleaning a wound utilizing ultrasonic energy.

A still further object of this invention is to a method of cleaning the prepared surface of a bone with a liquid containing ultrasonic energy that is released in direct contact with the surface of the bone.

An additional object of the present invention is the provision of a method of preparing and cleaning a bone for accepting a prothesis.

These and various other objects and advantages of the invention will become readily apparent to those skilled in the art upon reading the following detailed description and claims and by referring to the accompanying drawings.

The above objects are attained in accordance with the present invention by the provision of a method for use with apparatus fabricated in a manner substantially as described in the above abstract and summary.

BRIEF DESCRIPTION OF THE DRAWINGS

FIG. 1 is a side elevational view of an ultrasonic wound cleaner made in accordance with the present invention;

FIG. 2 is a side elevational, part cross-sectional view of the apparatus of FIG. 1;

FIG. 3 is a broken, cross-sectional, partly disassembled view of another embodiment of the apparatus disclosed in FIG. 1;

DETAILED DESCRIPTION OF THE PREFERRED EMBODIMENT

Figure 4:
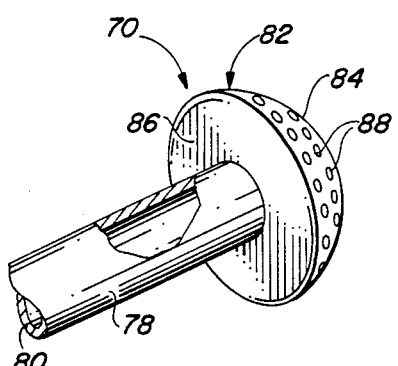
FIG. 4 is a broken, perspective view of part of the present invention with some parts being removed therefrom and the remaining parts shown in cross-section.

The figures of the drawings disclose an ultrasonic wound cleaner 10, made in accordance with the present invention, which includes a handle 12 to which there is attached an ultrasound transducer 14 having a collecting cone 15 that converges in opposition to the handle 12. The collecting cone 15 is suitably affixed to any number of applicators 16, such as the illustrated tube, which can be removed from cone 15 in order to mount different configurations of applicators thereto as will be more fully described later on herein.

Inlet tube 18 is connected to a suitable source of antibiotic solution. The antibiotic solution can be admixed with detergents, surfactants, and other surface tension modifying agents, so as to produce a frothing treatment liquid having great cleaning characteristics when used in accordance with this invention and which is hereinafter referred to as "antibiotic solution" or "treatment liquid". The flexible inlet tube 18 provides for a flow of treatment liquid through transducer 14 of this invention, with the liquid emerging at delivery ports 20 carrying ultrasonic or ultrasound energy therewith.

Flow control valve 22 can take on any number of different forms so long as it throttles or controls the flow of treatment liquid from tube 18, through transducer 14 and through the delivery ports 20 of applicator 16.

A hand pump 24, which can take on any number of different forms, is connected at 26 to a suitable flush solution. The flush solution can be a saline solution which is forced through the hand pump and through tubing 28, 30, 32. Tubing 28 is attached to handle 12 and extends about the transducer 14 where it circumvents collecting cone 15 and applicator 16. The terminal end 32 of the tubing 30 is open so that flow of flush solution can be achieved at a location in proximity of the lower depth of a wound.

The piezoelectric crystal that makes up the ultrasound transducer 14 is connected to a suitable power source by means of a conductor 34. Passageway 36 extends axially through transducer 14 by means of the central or axial passageway 38. Hence, transducer 14 is an annular transducer having an axial passageway through which liquid from tube 18 can flow while gathering ultrasonic energy. The interior 40 of collecting cone 15 converges toward an apex 42, or more exactly a frustum of a cone 15. Numeral 44 indicates the circumferentially extending outer peripheral wall surface of the transducer.

The apex 42 of the collecting cone 15 is internally threaded and thereby removably receives different cleaning applicators 16 thereon by which the treatment liquid, having ultrasound energy incorporated therein, is delivered directly to the interior surfaces that form the wound, thereby directly subjecting the interior of the wound to ultrasonic cleaning.

In FIG. 3, the applicator 16 is threaded at 48 and is made complementary respective to the threaded surface at apex 42 so that different configurations of applicator 16 can be substituted one for the other as is more particularly illustrated hereinafter.

Figure 6:
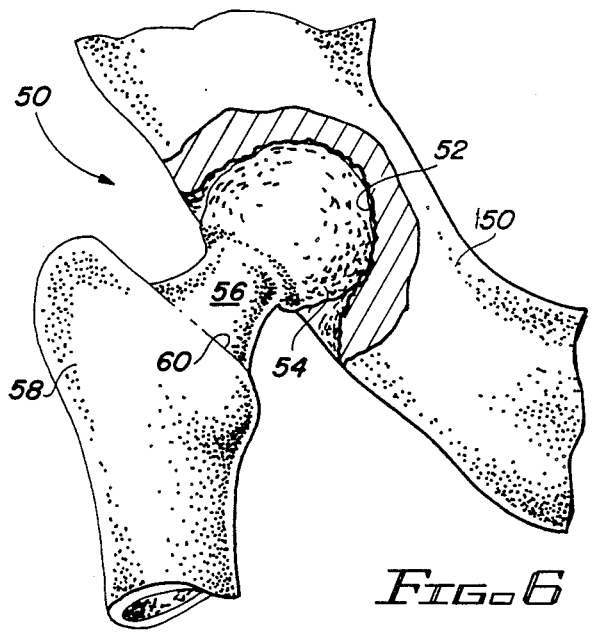
FIG. 6 is a broken view that sets forth part of the human anatomy on which the method of the present invention is practiced.

FIG. 6 discloses a human joint 50 comprising a pelvis having an acetabular fossa, hereinafter called a "socket", within which there is captured a femoral head 54 affixed to neck 56 which in turn is affixed to femur 58. The head 54 and socket 52 are damaged and therefore are about to be modified and thereafter replaced with a prosthesis whereby an artificial ball and socket, such as seen at 154, 152, respectively, in FIG. 10 will be substituted for the damaged ball and socket of FIG. 6.

Figure 10:
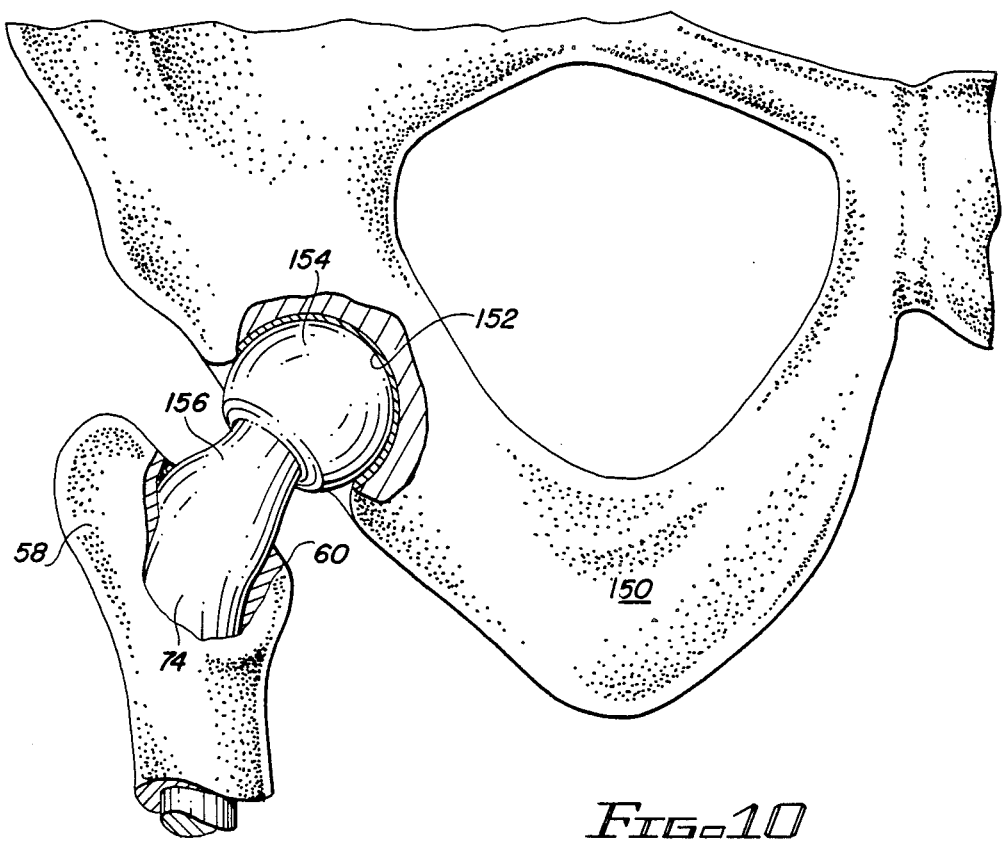

The femur 58 must therefore be dislocated from the pelvis, the neck 56 removed somewhere along level 60 which is the usual level for removal of a damaged femoral head and neck, and after proper treatment according to the present invention, a prosthesis is attached to the joint or pelvis 150 and the femur 58. The new head 154 is placed within new socket 152 as seen in FIG. 10.

Figure 8:
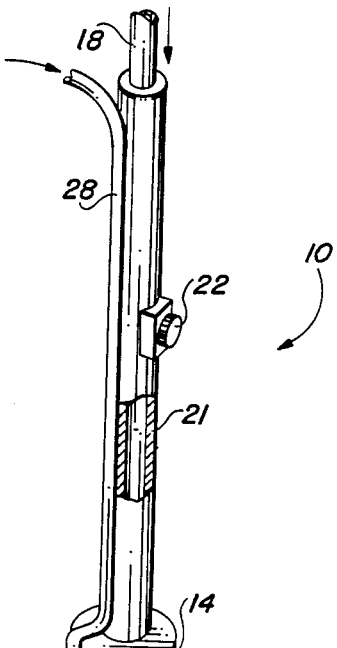
FIG. 8 is a part cross-sectional view showing another method of the present invention.
Figure 7:
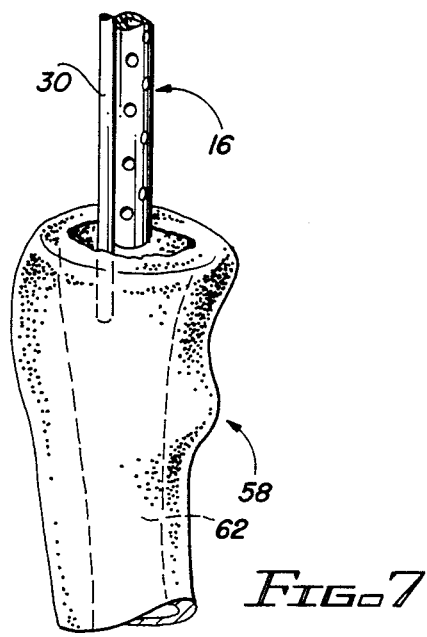
FIG. 7 is a fragmentary, representation of part of the apparatus previously disclosed in FIGS. 1 and 6.

In FIGS. 7 and 8, the femur 58 has a plateau formed along plane 60. Numeral 62 indicates the medullary canal of the femur while numeral 64 indicates that the medullary canal has been evacuated of all material leaving the sidewalls thereof which contain unwanted residual material that must be completely removed in order to expose the surface of the surrounding bone and thereby provide an optimal surface to be bonded to the components of the artificial joint. In FIG. 7, tissue that normally fills the medullary canal has been removed, and the medullary canal reamed with a suitably tapered reamer that is made complimentary respective to the appropriate parts of the prothesis which is to be mounted in the prepared canal. Applicator 16, along with the flush solution tube, is being extended down into the resultant open canal for the purpose of cleaning the canal of the residual tissue.

In FIG. 8, ultrasonic cleaning device 10 has been extended fully into the medullary canal so that the wall surface of the canal can be cleaned ultrasonically in accordance with the present invention.

Figure 5:
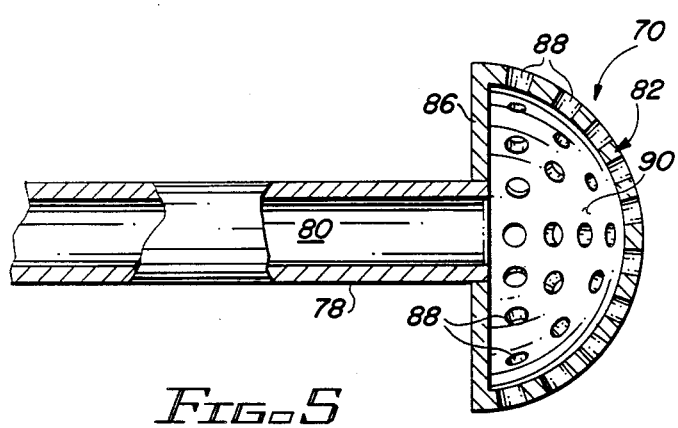
FIG. 5 is a broken, longitudinal, cross-sectional view of the apparatus disclosed in FIG. 4.
Figure 9:
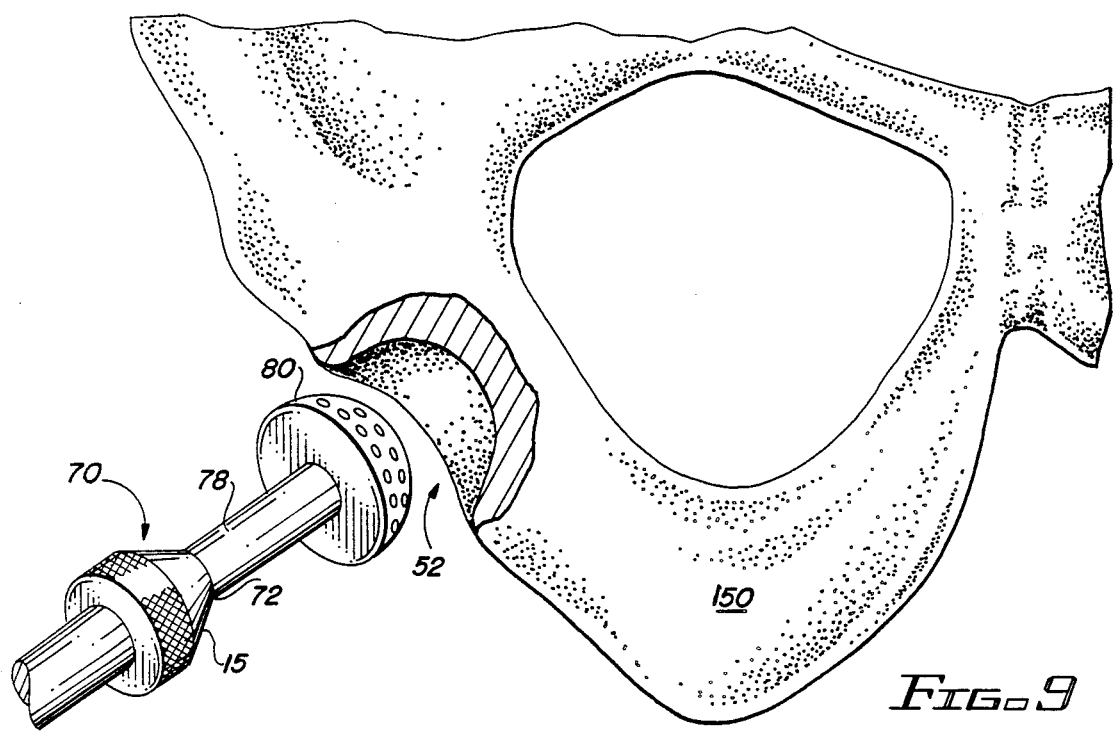
FIG. 9 shows part of the apparatus previously disclosed in FIG. 5, in conjunction with part of the human anatomy; and, FIG. 10 shows a total joint replacement that has been achieved in accordance with the present invention.

FIGS. 4, 5, and 9 illustrate another form of the present invention, wherein the applicator 16 is in the form of a mushroom shaped implement 70. An extension 78 attached at apex 42 of FIG. 3 forms a passageway 80 through which fluid can flow from interior 40 of collecting cone 15 into the mushroom shaped dispersing head 82. The dispersing head 82 has a curved outer wall 84 attached to bulkhead 86. Numeral 88 indicates randomly placed apertures for emergence of froth, or liquid containing ultrasonic energy. Numeral 90 indicates the interior of head 82.

In FIG. 10, the prosthesis has been installed in both the pelvis and the femur with there being a new socket 152 that captures head 154 which forms part of the prosthesis 156 and 74. The stem 74 extends into the cleaned medullary canal of the femur where it is suitably bonded thereto with methyl methacrylate cement.

OPERATION

In operation, an elongated delivery tube is threadedly affixed to threads apex 42 of collecting cone 15, the power source is connected at conductor 34, a source of antibiotic solution under pressure is made available within tubing 18, and a flush solution is made available at tubing 26.

After the medullary canal of the femur has been prepared and reamed, the applicator 16 is inserted into the resultant outwardly, opening canal 64 and valve 22 is opened to permit flow to occur from tube 18, axially through transducer 14, into the conical interior 40 where the transducer rapidly vibrates the liquid, causing the liquid to cavitate, froth, and thereby store ultrasonic energy. The treated liquid emerges from the delivery ports 20 and intimately contacts the sidewalls forming the medullary canal. As the liquid flows across the unwanted particles of material that cling to and is interposed between the bone and the applicator tube 16, ultrasonic energy is liberated from the liquid, shocking, vibrating, and acting upon the unwanted particles, causing the unwanted particles to be dislodged from adherence to the bone structure, whereupon the removed matter is floated out of the medullary canal and to disposal.

From time to time, hand pump 24 is squeezed in order to flush accumulated debris that has been removed from the surface of the canal. This procedure is completed when operation of the hand pump flushes very little debris from the canal because the canal has been cleaned of all unwanted matter.

Next, the surface of the canal is dried (made bone dry) so it will properly bond to stem 74 of the prosthesis when the two are cemented or bonded together. Simultaneously or sequentially, the mushroom cleaning head of FIGS. 4, 5, and 9 is substituted for applicator tube 16 so that the hip joint socket can be cleaned of unwanted matter left attached to the socket wall. In this instance, flow of antibiotic solution at tube 18 is throttled at control valve 22 as it flows axially through transducer 14, into collecting cone 15, along extension 78 and into interior 90 of head 82 where the liquid charged with ultrasonic energy emerges through apertures 88 and cleans the interior of the wound.

Next, socket 152 that surrounds ball joint 154 is similarly cemented into the hip joint socket 52 and the process is then completed.

The present invention provides an ultrasonic cleaning device 10 adapted to receive a different applicator 16 or implement thereon to facilitate cleansing of wounds and the cavities of bone as well as other parts of one's anatomy.

I claim:
1. An ultrasonic wound cleaning device comprising:
   an annular ultrasonic transducer having an axial bore extending therethrough;
   means for energizing said transducer to generate ultrasonic energy;
   a handle connected to one side of said transducer;
   a collecting cone having a base and an apex, said base being connected to the other side of said transducer;
   a cleaning applicator having upstream and downstream ends, said upstream end being removably connected to said apex of said collecting cone;
   said cleaning applicator being an elongated tubular member adapted to be extended into the open passageway of a wound and having perforations along the length of the downstream end; and
   means for providing flow of cleaning liquid through said axial bore of said transducer whereupon said cleaning liquid is subjected to ultrasonic energy and caused to cavitate, and then flow into the collecting cone, into the cleaning applicator, through the perforations of said cleaning applicator, and into the wound; the cleaning liquid releasing ultrasonic energy into the wound thereby cleaning the wound of unwanted matter.

2. The cleaning device of claim 1 further comprising:
   a source of flush liquid; and
   tubing means for conveying the flush liquid to the downstream end of said cleaning applicator whereby the flush liquid flushes the cleaning liquid from the interior of the wound,
   said tubing means having opposed ends, one end connected to the source of flush liquid and the other terminating at the downstream end of the cleaning applicator, said tubing means extending along the length of the cleaning applicator.

3. The cleaning device of claim 1 wherein said cleaning applicator is mushroom-shaped, having a hemispherical downstream end that is opposed to a bulkhead at the upstream end.

4. Method of cleaning a wound of unwanted matter using a cleaning device comprising an annular ultrasonic transducer; a collecting cone having a base and an apex, said base being connected to said transducer; a cleaning applicator removably connected to said apex of said collecting cone, the end of said cleaning applicator distal said collecting cone having a plurality of perforations; a cleaning liquid source connected to said transducer; means for energizing said transducer to generate ultrasonic energy; a flush liquid source; and flush liquid tubing, connected at one end to the flush liquid source, extending along the cleaning applicator to the perforated end, said method comprising the steps of:

directing the perforated end of the cleaning applicator toward the wound;

energizing said transducer with said means for energizing to generate ultrasonic energy;

flowing said cleaning liquid from the source through the transducer whereby ultrasonic energy is transferred into the cleaning liquid causing the cleaning liquid to cavitate;

flowing the energized cleaning liquid through the collecting cone, into the cleaning applicator, through the perforations, and into the wound thereby loosening unwanted matter from said wound; and flowing flush liquid through the tubing to flush any cleaning liquid and unwanted matter from the wound.

5. The method of claim 4, wherein the wound is a reamed canal in a bone; and further including the steps of making said cleaning applicator in the form of an elongated tubular member; and, extending the perforated end of the tubular member into the reamed canal of the bone, where the canal is subjected to the cleaning liquid flow from the perforated cleaning applicator and is thereby cleaned of unwanted matter.

6. The method of claim 4 wherein said cleaning applicator is mushroom-shaped, having a hemispherical downstream end that is opposed to a bulkhead at the upstream end.

7. Method of attaching a prosthesis to a bone using a cleaning device comprising an annular ultrasonic transducer; a collecting cone having a base and an apex, said base being connected to said transducer; a cleaning applicator removably connected to said apex of said collecting cone, the end of said cleaning applicator distal said collecting cone having a plurality of perforations; a cleaning liquid source connected to said transducer; means for energizing said transducer to generate ultrasonic energy; a flush liquid source; and flush liquid tubing, connected at one end to the flush liquid source, extending along the cleaning applicator to the perforated end, said method comprising the steps of:

removing an end of the bone and reaming the bone canal;

directing the perforated end of the cleaning applicator into the reamed canal;

energizing said transducer with said means for energizing to generate ultrasonic energy;

flowing said cleaning liquid from the source through the transducer whereby ultrasonic energy is transferred into the cleaning liquid causing the cleaning liquid to cavitate;

flowing the energized cleaning liquid through the collecting cone, into the cleaning applicator, through the perforations, and into the reamed canal thereby loosening unwanted matter from said reamed canal;

flowing flush liquid through the tubing to flush any cleaning liquid and unwanted matter from the reamed canal; and attaching the prosthesis to the reamed canal of the bone.

8. The method of claim 7 wherein said cleaning applicator is mushroom-shaped, having a hemispherical downstream end that is opposed to a bulkhead at the upstream end.

* * * * *